| United States Patent [19] | [11] Patent Number: 4,740,464 |
| Holdom et al. | [45] Date of Patent: Apr. 26, 1988 |

[54] FERMENTATION PROCESS AND MICROORGANISM FOR PRODUCING ACONITIC ACID

[75] Inventors: Kelvin S. Holdom, Ramsgate, England; Norman Winskill, Mount Kisco, N.Y.

[73] Assignee: Pfizer Inc., New York, N.Y.

[21] Appl. No.: 676,770

[22] Filed: Nov. 30, 1984

[30] Foreign Application Priority Data

Dec. 19, 1983 [GB] United Kingdom ................ 8333729

[51] Int. Cl.[4] .......................... C12N 1/14; C12P 7/62; C12P 7/48; C12R 1/66
[52] U.S. Cl. .................................. 435/135; 435/144; 435/254; 435/913
[58] Field of Search ............... 435/135, 136, 144, 254, 435/913

[56] References Cited

PUBLICATIONS

*Chemical Abstracts*, vol. 74, No. 25, Abstract 136821d; Jun. 21, 1971; Jakubowska et al., 'Identification of Organic Acids Occurring in Itaconic Fermentation'.
Sakaguchi and Baba, Bull. Ag. Chem. Soc., Japan 1942, 18, No. 12, 1127–1130, English Abstract 95.
Miller and Cantor, "Advances in Carbohydrate Chemistry", 1951, 6, 231–249.

*Primary Examiner*—Elizabeth Weimar
*Attorney, Agent, or Firm*—Peter C. Richardson; Lawrence C. Akers; J. Trevor Lumb

[57] ABSTRACT

Aconitic acid, an unsaturated tricarboxylic acid, is obtained by fermentation of an aconitic acid-accumulating strain of *Aspergillus terreus* or *Aspergillus itaconicus*, under aerobic conditions, in a carbohydrate-containing medium, followed by isolation of the aconitic acid or a salt thereof. A preferred aconitic acid-accumulating microorganism is the strain of *Aspergillus terreus* which is on deposit in the Culture Collection of the Commonewealth Mycological Institute at Kew, Surrey, United Kingdom, under Accession No. CMI CC 281924.

5 Claims, No Drawings

FERMENTATION PROCESS AND MICROORGANISM FOR PRODUCING ACONITIC ACID

BACKGROUND OF THE INVENTION

The invention relates to the production of aconitic acid and in particular to the production of aconitic acid by fermentation.

Aconitic acid is a naturally occurring acid being present in Aconitum and other genera of plants, including beet roots and sugar cane. It can be prepared from the calcium magnesium salt recovered from sugar cane juice and from molasses. Aconitic acid is also manufactured commercially by dehydration of citric acid. Aconitic acid is an intermediate of the tricarboxylic acid cycle and as such is produced by many microorganisms. However, it does not normally accumulate insignificant amounts. It has been alleged that aconitic acid is produced by fermentation of *Aspergillus niger* in the presence of methylene blue (Sakaguchi and Baba, Bull. Ag. Chem. Soc. Japan, 1942, 18, no. 12, 1127–1130, English abstract 95), but no fermentation process for the production of aconitic acid on a commercial scale has ever been developed.

Aconitic acid is an unsaturated tricarboxyic acid and is therefore potentially useful as a co-monomer which, by virtue of its carboxylic functionality, confers specific properties on polymeric materials in which it is incorporated. In the form of its esters, it also finds specialised use as a plasticiser for synthetic rubber and other polymeric materials such as polyvinyl chloride. However, such uses have not been very extensive, due to the high cost of manufacture. If a cheaper method of manufacture could be found, then such uses would become more attractive and further uses would become economic. A review of uses of aconitic acid has been published by Miller and Cantor, in "Advances in Carbohydrate Chemistry", 1951, 6, 231–249.

We have now discovered that certain mutant strains of *Aspergillus terreus* are capable of producing aconitic acid in good yield by fermentation of suitable carbohydrate substrates, including sucrose or glucose. Presently known strains of *Aspergillus terreus* produce predominantly itaconic acid from such substrates. We believe, moreover, that mutant strains of other itaconic acid producing Aspergillus species, e.g. *Aspergillus itaconicus,* could also be found which would be capable of producing aconitic acid in good yield.

We have also found that, if the production (or activity) of aconitase in the fermentation medium is inhibited, e.g. by adding a fluoroacetate, such mutant strains will produce citric acid in significant yield. Other methods of inhibiting the production (or activity) of aconitase would clearly have the same effect.

SUMMARY OF THE INVENTION

According to the present invention, therefore, there is provided a process for producing aconitic acid which comprises propagating an aconitic acid accumulating strain of *Aspergillus itaconicus* or *Aspergillus terreus* under aerobic conditions, in an aqueous carbohydrate-containing nutrient medium in which aconitase production is not inhibited, until significant quantities of aconitic acid have accumulated in the medium, and then recovering the aconitic acid or a salt thereof from the medium.

DETAILED DESCRIPTION OF THE INVENTION

One particularly useful aconitic acid accumulation strain of *Aspergillus terreus* has been produced by mutation from an itaconic acid producing strain in the Pfizer culture collection identified as M 490. This mutant strain (identified as M 141) was accepted for deposit for the purpose of patent procedure under the Budapest Treaty by the Culture Collection of the Commonwealth Mycological Institute at Kew, Surrey, in the United Kingdom, on Dec. 9, 1983, and is identified therein as CMI CC 281924. This strain produces predominantly aconitic acid with smaller quantities of other acis such as citric and isocitric acids. Typically the amounts of aconitic, citric and isocitric acids produced are in the ratio of about 92:3:5. No detectable quantities of itaconic acid are produced. Other mutant strains of *Aspergillus terreus* and of *Aspergillus itaconicus* can of course be used, the only criterion for their use in the present invention being that they accumulate predominantly aconitic acid, rather than itaconic acid or any other acid, by fermentation of suitable carbohdrate substrates.

*Aspergillus terreus* M 141 (CMI CC 281924) may be identified from the results obtained by growing it in various media as follows (all at 37° C. for 5 days):

Glucose/yeast extract/malt extract agar: heavy growth with abundant pale brown spores; reverse yellow-brown.
Czapek Dox agar: good growth with white aerial mycelium; some pale brown spores.
Potato/Dextrose Agar: thin growth with abundant dark brown spores.
Nutrient Agar: good growth; white aerial mycelium with sparse pale yellow spores.
Glycerol/mineral salts agar: good growth with abundant pale-brown spores.

At 28° C. growth was similar in all cases but spore production was generally less abundant.

The following carbon sources support growth (assayed after 48 hours at 37° C.): glucose, glycerol, 2-oxoglutarate, arabinose, xylose, xylitol, inositol, sorbitol, N-acetylglucosamine, cellobiose, lactose, maltose, saccharose, trehalose and raffinose. Weak growth is obtained on adonitol, galactose and melezitose whilst no growth occurs on methyl D-glucoside.

Acid production is observed after 48 hours growth at 37° C. on the following carbon sources: glucose, glycerol, L-arabinose, D-xylose, sorbitol, cellobiose, maltose, melezitose and raffinose, but no acid was produced from growth on D-arabinose, L-xylose, adonitol, galactose or N-acetyl glucosamine. Xylitol, inositol and trehalose supported weak acid production.

In all morphological and physiological tests conducted *Aspergillus terreus* M 141 (CMI CC 281924) was similar to the parent strain (M 490) from which it was derived, and to other strains of *A. terreus.* The important characteristic which distinguishes *A. terreus* M 141 (CMI CC 281924) and related strains covered by this invention is their ability to accumulate significant amounts of aconitic acid.

Aconitic acid exits as cis and trans isomers. Both forms occur naturally in plants in varying proportions, although it is known that it is the cis isomer which is formed in the Krebs tricarboxylic acid cycle in living organisms. The trans isomer is, however, the more stable from and, under suitable conditions of temperature and pH, the cis form isomerises and forms an equilibrium mixture with the trans isomer predominating. In the process of the present invention, therefore, the conditions of fermentation and recovery can influence the proportions of cis and trans isomers which are produced.

The aqueous fermentation medium used in the present invention contains a carbohydrate and nutrient materials for the strain of Aspergillus itaconicus or terreus used. The carbohydrate may be sucrose, maltose, glucose or any suitable source of these, such as potato or corn starch, dextrin or molasses. The nutrient materials include a source of assimilable nitrogen and inorganic salts. Of many nitrogen sources, corn steep liquor, wheat bran, soybean meal, cotton seed meal, urea, ammonium nitrate, sulphate or chloride, amino-acids, peptones and other enzymically digested proteins are suitable. Trace vitamins and essential minerals are often present as impurities in the crude carbohydrate and/or nitrogen sources, or may be added to the medium if necessary.

We have found that reducing the heavy metal content of some complex media, by techniques well known to those skilled in the art (see for example the reference in a review by L. M. Miall, in "Primary Products of Metabolism", Economic Microbiology Vol. 2, 47–119, ed. A. H. Rose, Academic Press London, 1978), gives increased yield of aconitic acid. Typically the levels of heavy metals such as manganese and iron are reduced to less than 5 ppm.

It has also been found that the inclusion of certain metabolic inhibitors in the medium, such as zinc salts, gives increased yields of aconitic acid. For example, $ZnSO_4 \cdot H_2O$ has proved to be effective when added at concentrations between 1 and 10 g/liter.

The Aspergillus itaconicus or terreus strains can be cultured at temperatures of from 28° to 42° C. at a pH in the range from 1.5 to 4.0 and good yields of aconitic acid are obtained after fermentation for 2 to 7 days. Inoculum is prepared by transferring cells of the strain grown on a suitable medium, such as malt agar containing 3% sodium chloride, to an aqueous nutrient medium containing a carbohydrate in a shaker flask. After shaking and incubating for a sufficient time at a suitable temperature, aliquots of this inoculum are then transferred to similar sterile media in fermenters which are stirred and aerated. This procedure may be repeated so that the cultures are pre-grown in several inoculum stages before being transferred to the production fermenter. The pH of the production media is maintained at a suitable level by addition of alkali, e.g. an aqueous solution of sodium hydroxide or ammonia or an aqueous suspension of calcium hydroxide or calcium carbonate.

When significant quantities of aconitic acid have accumulated, as shown by analysis of samples, the acid is then recovered from the media by methods well known in the art for the recovery of water-soluble organic carboxylic acids, e.g.,; filtration or centrifuging to remove cells of the micro-organism; concentration, e.g. by evaporation, to precipitate either aconitic acid or a salt thereof; or precipitation of the aconitic acid as an insoluble salt, e.g. the calcium salt, regeneration of the acid, e.g. with aqueous sulphuric acid, and separation and evaporation of the aqueous solution to yield the aconitic acid.

In order to determine aconitic acid in the fermentation medium to pH of the medium is first adjusted to 1.7 to 2.0 with hydrochloric acid or sulphuric acid then filtered or centrifuged to remove the fungal mycelium. The filtrate or supernatant liquid is then analysed by the following techniques:

(1) GAS CHROMATOGRAPHY

This provides a convenient means for separating and quantifying organic acids in fermentation media. The following method has been used for determining aconitic acid. The analysis is carried out with a Pye 104 gas chromatograph fitted with a flame ionization detector under the following conditions:

Column temperature: 148° C.
Detector temperature: 250° C.
Injector temperature: 148° C.
Helium flow rate: 30 ml/min
Hydrogen flow rate: 30 ml/min
Air flow rate: 500 ml/min A standard curve is first prepared by weighing out exactly about 10, 20, 40, 60 and 100 mg of aconitic acid and dissolving each in 10 ml of tetrahydrofuran (THF). Each sample is then treated in the following way: 0.2 ml of N,O-bis-(trimethylsilyl)-acetamide is added to 1 ml of the solution in a dry vial and the vial is quickly sealed with a PTFE faced disc and capped. The vial is heated at 100° C. for 1 hour. 1 Microliter of the clear supernatant is then injected onto the top of the column. A standard curve is prepared by plotting the amount of acid as abscissa and the corresponding peak area of the chromatogram as ordinate. The determination of the peak areas are conveniently calculated by means of an integrator attached to the gas chromatograph.

In order to assay fermentation broth filtrates, any residual carbohydrate must first be removed, as this may interfere with the subsequent analysis. This is achieved by passing 2 ml of the filtrate down a column containing 5 ml of IRA 68 anion exchange resin in the ammonium form. The organic acids in the filtrate adhere to the resin and the residual carbohydrate is removed by washing with 20 ml of water. The acids are then eluted from the resin with 5 ml of 20% w/v ammonia solution. 2 ml of this ammonia eluate are placed in a vial and heated in a water bath to remove the excess ammonia. The vial is then placed in a freeze drying carbinet until all of the water is removed. 1 ml of THF is added and the sample is treated as described above for the standard solutions.

The amount of aconitic acid in the sample is readily calculated by comparison with the standard curve. The amount of other acids present, such as itaconic acid, citric acid and isocitric acid, may be calculated in a similar manner.

(2) HIGH PERFORMANCE LIQUID CHROMATOGRAPHY (HPLC)

The aconitic acid content of broths can be assayed by injecting 10 microliters of sample into a HPLC chromatograph (Waters) operated under one of the following conditions. For method A broth filtrate of supernatant liquid may be injected directly. For method B the filtrate or supernatant is diluted at least 10 times with acetonitrile and filtered before injection.

Method A

Column: Partisil SAX (Whatmans) 30 cm×4 mm (internal diameter)
Solvent: 50/50 MeOH/0.08M aqueous $Na_2HPO_4$, adjusted to pH 6.6 with acetic acid
Flow rate: 2.0 ml/min Detector: UV detector operated at 230 nm (Cecil Instruments)
Retention time: cis Aconitic acid elutes after approx 5.1 mins, trans Aconitic acid elutes after approx 6.4 mins Method B Column: Lichrosorb diol, 10μ particle size (Merck) 30 cm×4 mm (internal diameter)
Solvent: 98/2 Acetonitrile/0.03M aqueous $H_3PO_4$
Flow rate: 1.6 ml/min
Detector: Refractive index (Waters) or UV detector operated at 200 nm (Cecil Instruments)
Retention time: Aconitic acid elutes after approx 4.7 mins.

The aconitic acid content of the sample is determined by integration of the relevant peak areas and comparison against standard mixtures containing accurately weighed amounts of aconitic acid treated as above. Method B can also be used to resolve aconitic acid from other acids such as citric acid, isocitric acid, malic acid and α-oxoglutaric acid.

(3) Acetic Anhydride-pyridine Method

This method, which is a modification of an original method described by M. Saffran and O. F. Denstedt in J. Biol. Chem., 175, 849 (1948), modified as described by J. M. Lowenstein in "Methods in Enzymology", volume XIII, p. 513 edited by J. M. Lowenstein, Academic Press (1969), has been used to determine aconitic acid. In the original method both citric acid and aconitic acid, as well as other interfering substances, reacted with acetic anhydride and pyridine to give coloured compounds which absorb at 425 nm. However, as pointed out by Lowenstein, if the reaction is carried out at 0° C. only aconitic acid is measured.

The following are Examples of the process of the invention:

EXAMPLE 1

(A) A first stage inoculum medium was prepared (in tap water) containing the following ingredients in the concentrations shown in g/liter:
mannitol: 50.0
$NaNO_2$: 2.0
$FeSO_4 \cdot 7H_2O$: 0.001
$Zn SO_4 \cdot 4H_2O$: 0.006
$CuSO_4 \cdot 5H_2O$: 0.0015
$CaCO_3$: 2.0
$MgSO_4 \cdot 7H_2O$: 1.0
$KH_2PO_4$: 2.4
nutrient broth powder (Oxoid): 0.1

One liter of this medium was placed in a 2.8 liter shaker flask (Fernbach) and sterilised by autoclaving at 15 psi for 20 minutes. The medium was inoculated by the addition of spores from a slant of *Aspergillus terreus* M 141 (CMI CC 281924) and shaken aerobically for 5 days at 32° C.

(B) A second stage inoculum medium was prepared by dissolving (in tap water) the following ingredients in the concentrations shown, in g/liter:
hydrolysed corn starch, treated to reduce its heavy metal content, glucose equivalent: 175
$KH_2PO_4$: 0.11
$MgSO_4 \cdot 7H_2O$: 2.1
$MnSO_4 \cdot 4H_2O$: 0.002
$CuSO_4 \cdot 5H_2O$: 0.018
$NH_4NO_3$: 2.1

2.5 Liters of this medium was placed in a 5 liter fermenter and sterilised by autoclaving at 15 psi for 20 mins. The sterile medium was inoculated with 100 ml of 1st stage inoculum broth grown as described in (A) and further incubated for 28 hours at 30° C. with aeration (2.0 liters/min) and agitation (1500 rpm).

(C) A third stage inoculum was prepared by dissolving (in tap water) the following ingredients in the concentrations shown in g/liter:
hydrolysed corn starch, treated to reduce its heavy metal content, glucose equivalent: 175
$KH_2PO_4$: 0.1
$MgSO_4 \cdot 7H_2O$: 2.0
$CuSO_4 \cdot 5H_2O$: 0.2
$NH_4NO_3$: 2.0
$CaCO_3$: 1.0
sodium glutamate: 5.0

2.5 Liters of this medium was placed in a 5 liter fermenter and sterilised as above. The sterile medium was inculated with 400 mls. of second stage inoculum broth grown as described in (B) and further incubated for 24 hours at 30° C. with aeration (2.0 liters/min) and agitation (1500 rpm).

(D) A production stage medium was prepared by dissolving (in tap water) the following ingredients in the concentrations shown, in g/liter:
glucose (Cerelose): 200
$KH_2PO_4$: 0.25
$MgSO_4 \cdot 7H_2O$: 2.0
$NH_4NO_3$: 3.0
$ZnSO_4 \cdot H_2O$: 4.0

2.5 liters of this medium was placed in a 5 liter fermenter and sterilised as above.

The sterile medium was inoculated with 200 mls of third stage inoculum broth grown as described in (C) and further incubated for 120 hours (5 days) with aeration (2 liters/min) and agitation (1500 rpm). The temperature was controlled at 35° C. for the first 4 hours and then at 41° C. and the pH was controlled to pH 4.0 by the addition of aqueous sodium hydroxide. The final broth contained 50.1 g/liter of aconitic acid.

EXAMPLE 2

The procedures of Example 1 were repeated except that sucrose (200 g/liter) was used in the production medium in place of glucose. The final broth contained 52.0 g/liter of aconitic acid.

EXAMPLE 3

The procedures of Example 1 were repeated except that the production medium contained the following ingredients in the concentrations shown in g/liter:
hydrolysed corn starch, treated to reduce its heavy metal content, glucose equivalent: 250
$KH_2PO_4$: 0.2
$ZnSO_4 \cdot H_2O$: 5.0

The final broth contained 100.5 g/liter of aconitic acid.

EXAMPLE 4

The procedures of Example 1 were repeated except that $ZnSO_4 \cdot H_2O$ was omitted from the production medium. The final broth contained 45.1 g/liter of aconitic acid.

EXAMPLE 5

The procedures of Example 3 were repeated but an aqueous suspension of calcium hydroxide was used in place of aqueous sodium hydroxide to control pH in the production medium. The final broth contained 79.6 g/liter of aconitic acid.

EXAMPLE 6

A production medium was prepared by dissolving 0.25 g/liter $KH_2PO_4$ and 4.0 g/liter $ZnSO_4 \cdot H_2O$, in 2.5 liters of an aqueous solution containing 220 g/liter of sucrose treated to reduce its heavy metal content. The medium was placed in a 5 liter fermenter and sterilised by autoclaving at 15 psi for 20 mins. The sterile medium was inoculated with 200 ml of a first stage inoculum broth grown as described in Example 1(A). The production stage was run as described in Example 1(D) except that an aqueous suspension of calcium hydroxide was used to control the pH instead of aqueous sodium hydroxide. The final broth contained 82.9 g/liter of aconitic acid.

Aconitic acid, as free acid or as its sodium salt, is recovered from the final broths in each of Examples 1 to 6 by the following procedures:

EXAMPLE 7

Sodium aconitate was recovered from the final broths prepared in Examples 1 to 4 by filtration of the whole broth with a silicaceous filter aid to remove the cells, concentration of the filtrate containing sodium aconitate by evaporation, and recrystallisation of the crude product from water (yield 50-60%).

EXAMPLE 8

Aconitic acid is recovered from final broths prepared as in Examples 1 to 4 by filtration as in Example 7, removal of the sodium by passing the filtrate down a column of ion exchange resin (Amberlite IRC 50 in the acid form) and eluting the aconitic acid with water. The eluant from the column containing the aconitic acid is then further treated as for the filtrate in Example 7 (yield 50-60%).

EXAMPLE 9

Aconitic acid is recovered from final broths as prepared in Examples 5 and 6 by acidification of the broth to pH 1.0 to 3.0, (typically 1.9) by the addition of sulphuric acid, filtration to remove cells and precipitated calcium sulphate and concentration of the filtrate by evaporation. The crude material is then treated with activated carbon to remove colour, and the aconitic acid is recrystallised from water (yield 24%).

What is claimed is:

1. A process for producing aconitic acid or a salt thereof which comprises propagating a microorganism selected from *Aspergillus terreus* CMI CC 281924 and mutants thereof, under aerobic conditions, in an aqueous fermentations medium containing a carbohydrate and a source of assimilable nitrogen and inorganic salts, until at least about 45 g/liter of aconitic acid has accumulated in the medium.

2. The process according to claim 1, wherein said microorganism is *Aspergillus terreus* CMI CC 281924.

3. The process according to claim 2, which includes the further step of recovering the aconitic acid or a salt thereof from the medium.

4. A biologically pure culture of a microorganism selected from *Aspergillus terreus* CMI CC 281924 and mutants thereof, said microorganism being an aconitic acid-accumulating strain when propagated under aerobic conditions, in aqueous fermentation medium containing a carbohydrate and a source of assimilable nitrogen and inorganic salts.

5. A biologically pure culture according to claim 4 wherein said microorganism is *Aspergillus terreus* CMI CC 281924.

* * * * *